United States Patent
Park, Jr. et al.

(10) Patent No.: US 10,462,893 B2
(45) Date of Patent: Oct. 29, 2019

(54) METHOD AND SYSTEM FOR SURFACE MODIFICATION OF SUBSTRATE FOR ION BEAM TARGET

(71) Applicant: Neutron Therapeutics, Inc., Danvers, MA (US)

(72) Inventors: William H. Park, Jr., Marblehead, MA (US); Mark Lambert, South Hamilton, MA (US); Joseph Gillespie, Boxford, MA (US); Noah Smick, Winchester, MA (US); Takao Sakase, Rawley, MA (US)

(73) Assignee: NEUTRON THERAPEUTICS, INC., Danvers, MA (US)

( * ) Notice: Subject to any disclaimer, the term of this patent is extended or adjusted under 35 U.S.C. 154(b) by 140 days.

(21) Appl. No.: 15/613,961

(22) Filed: Jun. 5, 2017

(65) Prior Publication Data
US 2018/0352643 A1    Dec. 6, 2018

(51) Int. Cl.
*H05H 6/00* (2006.01)
*G21G 4/02* (2006.01)

(52) U.S. Cl.
CPC ............. *H05H 6/00* (2013.01); *G21G 4/02* (2013.01)

(58) Field of Classification Search
CPC .. H05H 6/00; H05H 3/06; G21G 4/00; G21G 4/02
See application file for complete search history.

(56) References Cited

U.S. PATENT DOCUMENTS

| | | | | |
|---|---|---|---|---|
| 5,392,319 A | * | 2/1995 | Eggers | H05H 3/06 376/151 |
| 9,974,979 B2 | | 5/2018 | Liu et al. | |
| 2005/0135533 A1 | * | 6/2005 | Le Tourneur | H05H 3/06 376/114 |
| 2012/0307950 A1 | | 12/2012 | Sekine et al. | |
| 2013/0279638 A1 | * | 10/2013 | Matsumoto | G21G 4/02 376/108 |
| 2015/0216029 A1 | * | 7/2015 | Tsuchida | H05H 6/00 376/151 |
| 2016/0270202 A1 | * | 9/2016 | Shioda | H05H 6/00 |

(Continued)

FOREIGN PATENT DOCUMENTS

| | | |
|---|---|---|
| CN | 204667894 | 9/2015 |
| CN | 205462125 | 8/2016 |

(Continued)

OTHER PUBLICATIONS

International Search Report and Written Opinion on PCT Application No. PCT/US2017/035962, dated Apr. 17, 2018. 12 pages.

*Primary Examiner* — Sharon M Davis
(74) *Attorney, Agent, or Firm* — DLA Piper LLP (US)

(57) ABSTRACT

Design and making methods of a neutrons generating target are described. In some embodiments, a surface of a target substrate can be modified to form one or more surface features. In some embodiments, a neutron source layer can be disposed on the surface of the target substrate. In some embodiments, the neutron source layer and the target substrate can be heated to an elevated temperature to form a bond between the two. In some embodiments, the surface modification of the target substrate can reduce blistering and material exfoliation in the target. The target can be used in boron neutron capture therapy.

20 Claims, 7 Drawing Sheets

(56) References Cited

U.S. PATENT DOCUMENTS

| | | |
|---|---|---|
| 2017/0062086 A1 | 3/2017 | Park, Jr. et al. |
| 2018/0001112 A1 | 1/2018 | Liu et al. |
| 2018/0114605 A1 | 4/2018 | Chang et al. |
| 2018/0155368 A1 | 6/2018 | Li et al. |

FOREIGN PATENT DOCUMENTS

| | | | | |
|---|---|---|---|---|
| CN | 205722821 | | 11/2016 | |
| CN | 106621071 | | 5/2017 | |
| JP | 2014081211 | * | 5/2014 | ............... H05H 3/06 |
| JP | 2015-095365 | | 5/2015 | |
| WO | 2009/108906 | | 9/2009 | |
| WO | 2017/054548 | | 4/2017 | |
| WO | 2017/054556 | | 4/2017 | |
| WO | 2017/054557 | | 4/2017 | |
| WO | 2017/063407 | | 4/2017 | |
| WO | 2017/080344 | | 5/2017 | |
| WO | 2017/084459 | | 5/2017 | |
| WO | 2017/088606 | | 6/2017 | |
| WO | 2017/097035 | | 6/2017 | |
| WO | 2017/114316 | | 7/2017 | |
| WO | 2017/114317 | | 7/2017 | |
| WO | 2017/118291 | | 7/2017 | |
| WO | 2017/121337 | | 7/2017 | |
| WO | 2017/162093 | | 9/2017 | |
| WO | 2017/181791 | | 10/2017 | |
| WO | 2017/206485 | | 12/2017 | |
| WO | 2018/006551 | | 1/2018 | |
| WO | 2018/076787 | | 5/2018 | |
| WO | 2018/076790 | | 5/2018 | |
| WO | 2018/086367 | | 5/2018 | |

* cited by examiner

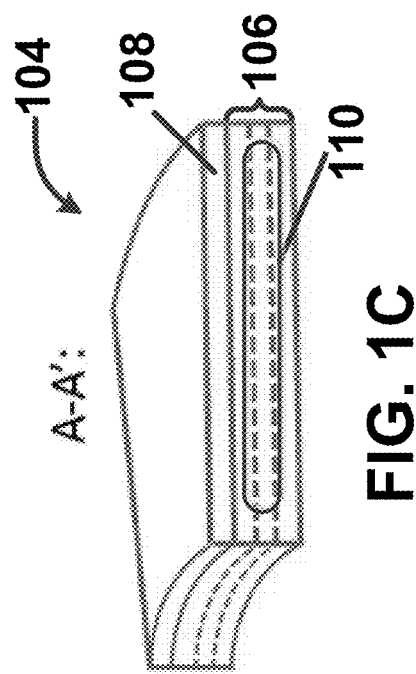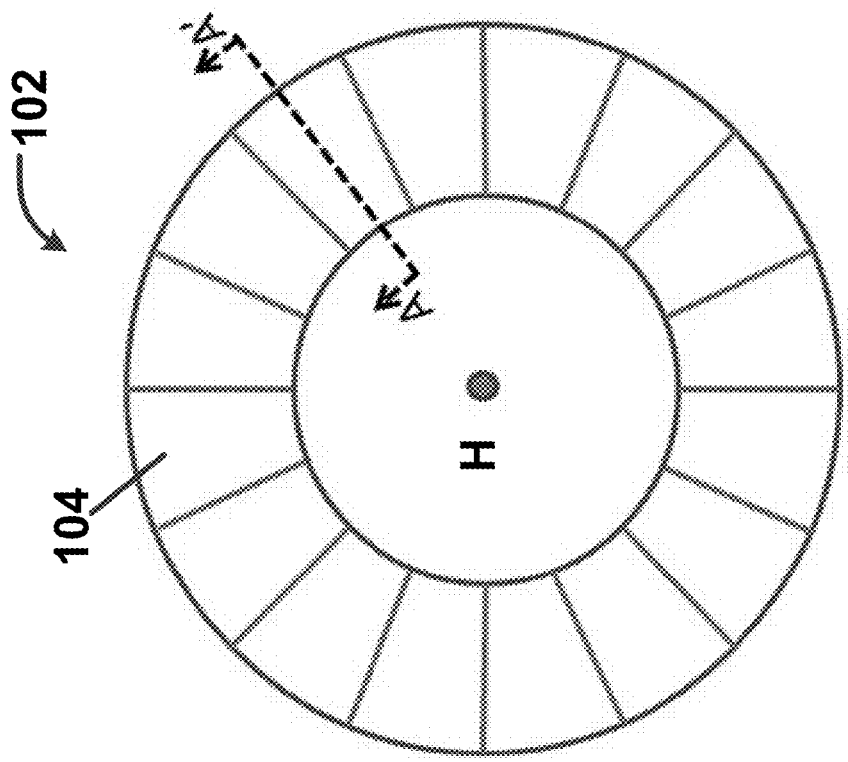

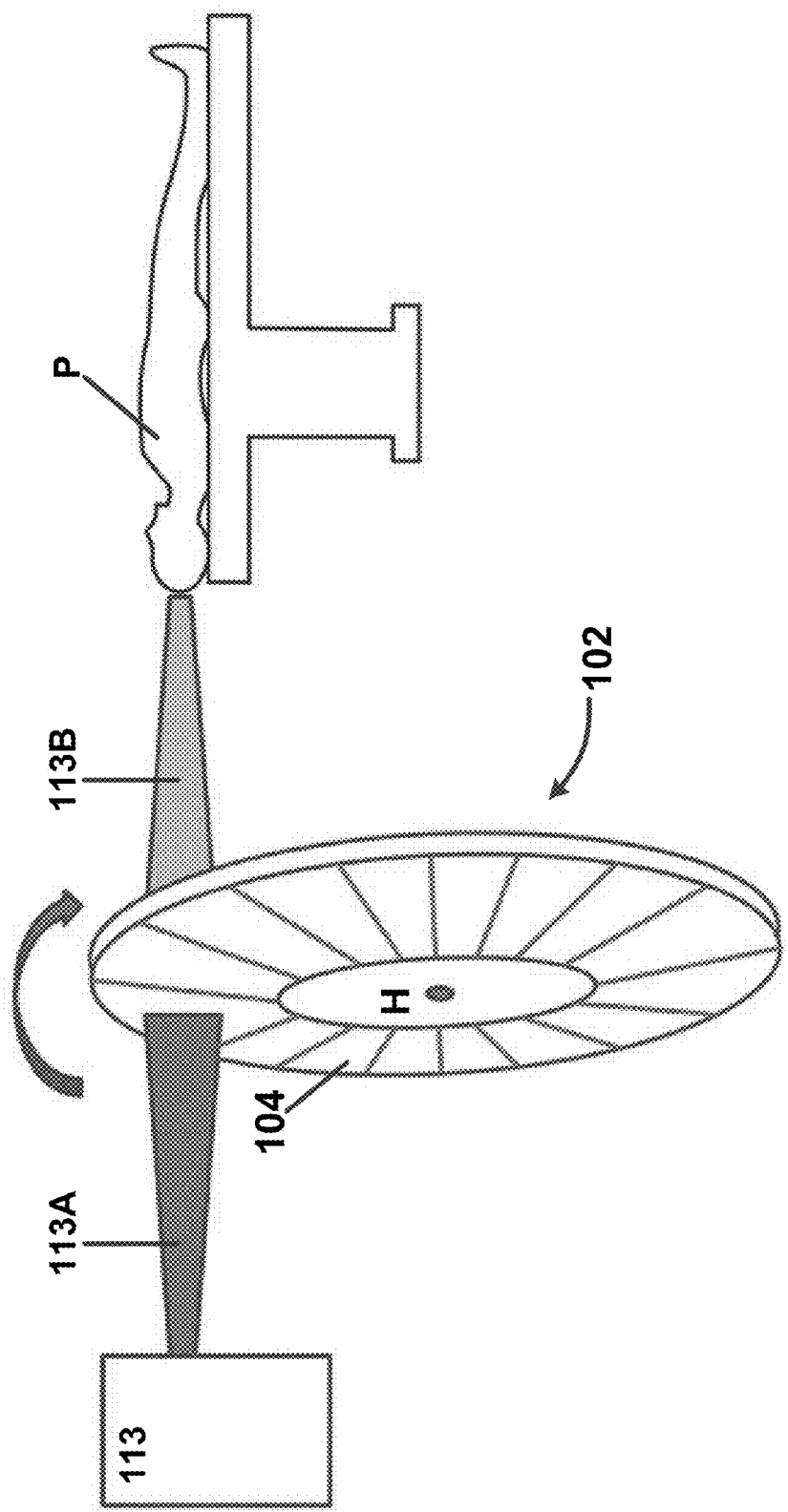

METHOD AND SYSTEM FOR SURFACE MODIFICATION OF SUBSTRATE FOR ION BEAM TARGET

CROSS-REFERENCE TO RELATED APPLICATIONS

This application relates to U.S. patent application Ser. No. 15/147,565, filed on May 5, 2016, the disclosure of which is incorporated by reference herein in its entirety.

FIELD

The present disclosure generally relates to design and making method of a neutron generating target which can be used in boron neutron capture therapy.

BACKGROUND

Neutron sources have many potential applications, including medical treatments, isotope production, explosive/fissile materials detection, assaying of precious metal ores, imaging, and others. A particular area of interest is boron neutron capture therapy (BNCT), which is a cancer treatment technique in which boron is preferentially concentrated in a patient's malignant tumor and a neutron beam is aimed through the patient at the boron-containing tumor. When the boron atoms capture a neutron, particles are produced having sufficient energy to cause severe damage to the tissue in which it is present. The effect is highly localized, and, as a result, this technique can be used as a highly selective cancer treatment method, effecting only specifically targeted cells.

Many activities employing neutron sources are presently carried out at nuclear research reactors where neutrons are plentiful. However, many practical issues such as safety, nuclear materials handling, and the approach of end-of life and decommissioning of many research reactors make this approach challenging. Accelerator-based neutron sources can be used as a relatively low-cost, compact alternative. For example, a small, relatively inexpensive linear accelerator can be used to accelerate ions, such as protons, which can then be focused on a target capable of generating neutrons.

SUMMARY

The present disclosure relates to a method for making a neutron generating target. The method can include modifying a surface of a target substrate to form one or more surface features. The method can also include disposing a neutron source layer on the surface of the target substrate.

In some embodiments, the method can include a material removal process or a material addition process. The material removal process can include abrasive blasting, etching, or polishing. The material addition process can include vacuum deposition, plating, or printing.

In some embodiments, the target substrate can include at least one of copper, aluminum, titanium, molybdenum, and stainless steel. The neutron source layer can include at least one of lithium, beryllium, and carbon.

In some embodiments, the neutron source layer can be pressed on the surface of the target substrate. In some embodiments, the neutron source layer can be deposited on the surface of the target substrate by evaporation.

In some embodiments, the method can include heating the neutron source layer and the target substrate to an elevated temperature for a duration of time for form a bond between the neutron source layer and the target substrate. In some embodiments, the elevated temperature can be between about 100 degrees Celsius and about 500 degrees Celsius. In some embodiments, the duration of time can be between about 0.1 hours and 10 hours.

In some embodiments, the method can also include modifying a top surface of the neutron source layer to form one or more surface features.

The present disclosure also relates to a neutron generating target. The target can include a target substrate having an uneven surface. The uneven surface can include one or more surface features. The target can also include a neutron source layer disposed on the surface of the target substrate and bonded to the target substrate.

In some embodiments, the one or more surface features can be recessed into the target substrate. The one or more surface features can have a depth of between about 1 micron and about 50 microns.

In some embodiments, the one or more surface features can protrude from the target substrate. The one or more surface features can have a height of between about 1 micron and about 50 microns.

In some embodiments, the one or more surface features can include a plurality of surface features with an average pitch of between about 1 micron and about 50 microns.

In some embodiments, the target substrate can include at least one of copper, aluminum, titanium, molybdenum, and stainless steel. The neutron source layer can include at least one of lithium, beryllium, and carbon.

In some embodiments, the neutron source layer can have a thickness of between about 10 microns and about 500 microns.

BRIEF DESCRIPTION OF THE DRAWINGS

Specific embodiments of the present disclosure are described below and shown in FIGS. 1-5. These embodiments are being presented by way of example only. Numerous modifications and other embodiments are within the scope of one of ordinary skill in the art and are contemplated as falling within the scope of the present disclosure. In addition, those skilled in the art should appreciate that the specific conditions and configurations are exemplary and that actual conditions and configurations will depend on the specific system. Those skilled in the art will also be able to recognize and identify equivalents to the specific elements shown, using no more than routine experimentation.

FIG. 1B is a diagram of a plan view of a disk-shaped rotatable structure, in accordance with some embodiments of the present disclosure.

FIG. 1C is a diagram showing a cross-sectional view of the rotatable structure of FIG. 1B, corresponding to line A-A' of FIG. 1B.

FIG. 1D is a diagram of the rotatable structure of FIG. 1B during use as part of boron neutron capture therapy (BNCT), in accordance with some embodiments of the present disclosure.

DETAILED DESCRIPTION

Figure 1A:
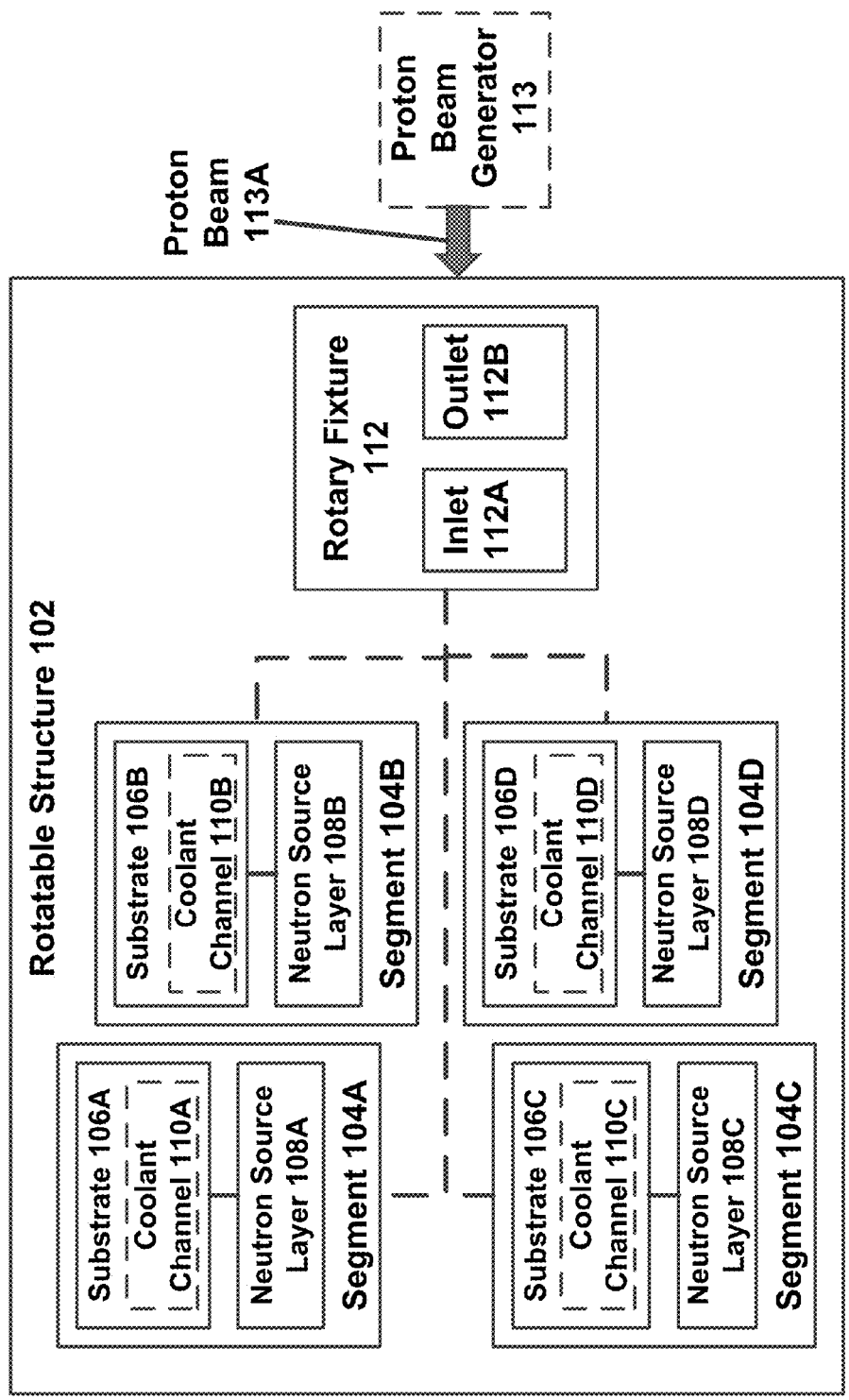
FIG. 1A is a block diagram of an apparatus suitable for use in boron neutron capture therapy (BNCT), in accordance with some embodiments of the present disclosure.

The present disclosure relates to design and manufacture method of a neutron generating target which can be used in boron neutron capture therapy (BNCT).

BNCT is a targeted radiation therapy for cancer treatment during which a patient is infused with a boron rich solution such as fructose-BPA. The boron is then selectively absorbed by the cancer cells, e.g., at a tumor site. Neutrons, for example, generated by a lithium neutron source, interact with the boron by the nuclear reaction: $^{10}B+n_{th} \rightarrow [^{11}B]^{*}\alpha+^{Li}+2.31$ MeV. By irradiating the patient's tumor site with a flux of epithermal neutrons, which thermalize near the tumor site, the cancer cells are killed by the alpha particles and lithium ions. The alpha particles and lithium ions released have very short ranges, for example about 5-9 microns, and thus are similar in size to a cancer cell.

BNCT treatment requires a high flux of epithermal neutrons, typically between 1 eV and 10 keV. Fluxes required for clinical treatments are on the order of $1 \times 10^9$ n/cm$^2$/s. Historically, BNCT treatments have been performed at nuclear research reactor facilities, however accelerator-based neutron sources are preferred for widespread implementation of the treatment in hospital environments.

To produce the appropriate level of neutron flux using an accelerator, several nuclear reactions have been proposed. One of the most promising reactions is the $^{7}$Li(p,n)$\rightarrow^{7}$Be reaction. This reaction has a high neutron yield and produces neutrons of modest energy, both conditions being desirable for many applications. The neutron flux produced by this reaction is desirable for BNCT, for example because the flux can be easily moderated to epithermal neutrons without many high energy neutrons. To accomplish this reaction with an accelerator-based neutron source, a target bearing a source material (e.g., lithium) is presented to a proton beam generated by the proton accelerator. Neutrons are emitted from the source material and may be moderated and collimated by a beam shaping assembly into the desired neutron "beam" for treatment. The proton beam size can be of comparable size or smaller size than the neutron beam at the exit of the beam shaping assembly. For example, the proton beam size can be between about 20 mm and about 150 mm. There are two general approaches to the lithium P,N reaction for BNCT: "near threshold," where the proton beam energy is about 1.9 MeV, and "above threshold," where the proton beam energy is about 2.5 MeV. The "near threshold" approach has the advantage that the neutron energy distribution from the target is close to the epithermal energy distribution for treatment, thus only minimal moderation can be used. The "above threshold" approach produces a higher energy distribution of neutrons, and therefore can use more moderation, but takes advantage of a large peak in the reaction cross section at about 2.3 MeV resulting in a much higher initial yield of neutrons.

Embodiments of the present disclosure overcome the neutron generation system issues described above using a direct-cooled, modularized rotating target architecture approach. For example, in some embodiments, a rotatable structure such as a disk or a drum includes a plurality of segmented target "petals" (also referred to herein as "segments") attached to a central hub (also referred to herein as a "rotary fixture"), where each petal is directly cooled via its own dedicated micro-channels. The plurality of target petals, collectively, may be said to constitute a target. Each petal can include a substrate and a solid neutron source layer disposed on a surface of the substrate. An exemplary system includes 16 petals on a planar rotatable structure, each petal occupying 22.5 degrees of a circumference of the rotatable structure, with the rotatable structure having an outer diameter (OD) of about 1 meter, and a semi-continuous strip of lithium deposited on the petals 0.14 meters in the radial direction centered on a 0.84 meter diameter.

FIG. 1A is a block diagram of an apparatus suitable for use in BNCT, in accordance with some embodiments of the present disclosure. As shown in FIG. 1A, a rotatable structure 102 includes a plurality of target petals or segments 104A-104D, and each segment of the plurality of segments 104A-104D has a corresponding substrate 106A-106D coupled to a corresponding neutron source layer 108A-108D. The neutron source layer(s) 108A-108D can include solid lithium. One or more of the substrates 106A-106D includes a corresponding coolant channel (110A-110D), such as a micro-channel, for actively cooling the associated substrate and/or neutron source layer (e.g., to maintain the neutron source layer 108A-108D in solid form). The segments 104A-104D are optionally coupled to a rotary fixture 112 having an inlet 112A and an outlet 112B for conducting a coolant fluid. The segments 104A-104D can be coupled to the rotary fixture 112 via one or more of: screws, bolts, quick-disconnect fittings, clamps, and/or the like. The coolant fluid can include one or more of: water (e.g., deionized water, which provides higher heat capacity and thermal conductivity than oils, and lower corrosive activity as compared with city water), glycol, a glycol/water mixture, heat transfer oils (e.g., to avoid possible water/lithium interaction during a failure), "Galinstan" (a commercial liquid gallium/indium/tin mixture), liquid nitrogen, and/or other coolants. The rotary fixture 112 can be configured to couple to an external spindle assembly and/or drive motor via a coupling such as a rotary water seal and/or a rotary vacuum seal. When the segments 104A-104D are connected to the rotary fixture 112, the coolant channels 110A-110D may be in sealed fluid communication with the inlet 112A and outlet 112B of the rotary fixture 112. FIG. 1A also depicts a proton beam generator 113 and a proton beam 113A.

Each segment of the segments 104A-104D can have a shape that is one of: a portion of an annulus, a pie-shape or "sector" (defined as the plane figure enclosed by two radii of a circle or ellipse and the arc between them), a truncated sector (i.e., a portion of a sector), a square, and a rectangle.

The neutron source layer 108A-108D can include lithium, beryllium, or another suitable neutron source in solid form and at a thickness that is sufficient to produce the desired neutron flux, for example for lithium at least about 10 µm, or at least about 90 µm (e.g., about 400 µm), or between about 10 µm and about 200 µm, or between about 90 µm and about 150 µm.

The neutron source layer 108A-108D can be adhered to the substrates 106A-106D of the segments 104A-104D via a thermal bond. For example, in some embodiments, one or more of the substrates 106A-106D include copper, and a lithium neutron source layer 108A-108D is bonded to the one or more copper substrates 106A-106D via a pressure and temperature method. As lithium is a reactive metal, it can form an amalgam with the copper. When properly bonded, a low thermal resistance between the copper and the lithium is formed. At such thicknesses of the neutron source layer(s) 108A-108D, the protons are deposited in the lithium during use, as opposed to the copper that underlies the lithium. In some cases, there is no drop in neutron yield up to doses of $1\times10^{19}$ ions/cm$^2$, and it can be expected that doses of $1\times10^{20}$ ions/cm$^2$ and beyond are possible. The neutron source layer 108A-108D can change during irradiation, for example becoming more brittle and/or different in color, however as long as it remains intact and produces the same or nearly the same neutron yield, it is suitable for use.

Alternatively or in addition, the neutron source layer 108A-108D can be evaporated onto the substrates 106A-106D in a thin layer, for example of about 100 microns. A very thin, blister-resistant middle layer can be included in such designs as well (as has done in the stationary targets, described above). The base petal or substrate can be made of copper or aluminum. Even materials such as stainless steel, titanium, and molybdenum are possible since the distributed heat power is so much lower than in the stationary case.

FIG. 1B is a diagram of a plan view of a disk-shaped rotatable structure, in accordance with some embodiments. As shown, the rotatable structure 102 has a central hub portion "H" with a plurality of segments 104 attached thereto and emanating therefrom. The segments 104 each include a corresponding neutron source layer with a major surface that can be, for example, substantially normal to an axis of rotation of the rotatable structure 102. The axis of rotation may be defined as an axis that passes through the center of the hub "H" and is substantially normal thereto. FIG. 1C is a diagram showing a cross-sectional view of the rotatable structure of FIG. 1B, corresponding to line A-A' of FIG. 1B. As shown in FIG. 1C, a neutron source layer 108 is disposed on a substrate 106 with an embedded coolant channel 110.

FIG. 1D is a diagram of the rotatable structure of FIG. 1B during use as part of boron neutron capture therapy (BNCT), in accordance with some embodiments. As shown, the rotatable structure 102 is rotating about its axis of rotation, and a proton beam generator 113 emits a proton beam 113 toward the rotatable structure 102 such that the proton beam 113A contacts a surface of the rotatable structure 102, e.g., at a neutron source layer of a segment 104. The proton beam 113A can be stationary (e.g., at a predetermined position) or rastering over a predetermined region of the rotatable structure 102, where the predetermined region may be fixed or may change over time. The proton beam 113A can form an angle with the contacting surface of the rotatable structure 102, for example of about 90.degree. Since the rotatable structure 102 is rotating, segments 104 of the rotatable structure 102 can be sequentially contacted by the proton beam 113A. As a result of the interaction of the proton beam 113A with the neutron source layer of segment(s) 104, a neutron beam 113B is generated and directed (e.g., via a collimator or other beam-shaping structure) towards a treatment area of a patient P.

One major failure mode of the neutron generating target in the art is hydrogen impregnation within the target. The hydrogen deposited in the target may damage the target materials, cause blistering of the target, limit the lifetime of the target, and necessitate servicing of the target prior to failure. Blistering is material damage (e.g., delamination, exfoliation, bubble, etc.) in the target due to internal hydrogen pressure exceeding the strength of the target material. When the proton beam hits the target, the depth where the protons stop depends on the energy of the proton and the neutron source material. For example, in a target with a thick lithium neutron source layer (about 400 µm) bonded to a copper substrate, a 2.6 MeV proton beam may be stopped in the lithium layer. Instead, if a thinner lithium neutron source layer (between about 100 µm and about 200 µm) is used, the proton beam may be stopped in the copper layer. When the hydrogen concentration reached a point where internal pressure exceeds the strength of the material, a blistering might happen. The blistering can happen in the lithium layer or in the copper layer.

The present disclosure provides a target design which significantly reduces target blistering failure. In the target used in the art, the surface of the target substrate is substantially flat and neutron source materials are bonded on the top surface of the target substrate. Protons with similar energies will stop in the target at a same depth. As a result, hydrogen concentration may become high at this depth and lead to target damage.

The present disclosure shows a different target design where the surface of the target substrate is modified. In some embodiment, the target substrate can be copper, aluminum, titanium, stainless steel, or other metals. The goal of the surface modification is to increase the roughness of the target substrate.

In some embodiments, the target substrate can be modified with a material removal process. For example, the substrate can be modified with abrasive blasting. Different blasting media can be used in accordance with roughness requirements and substrate materials. In some embodiments, the blasting media can be sand, silicon dioxide, metal shot, etc. The substrate can also be modified by etching or polishing.

In some embodiments, the target substrate can also be modified with a material addition process. For example, a thin layer of material can be added to the target substrate surface by vacuum deposition, plating, printing, or other techniques. In some embodiments, the material to be added can be copper, aluminum, titanium, stainless steel, or other metals.

Figure 2A:
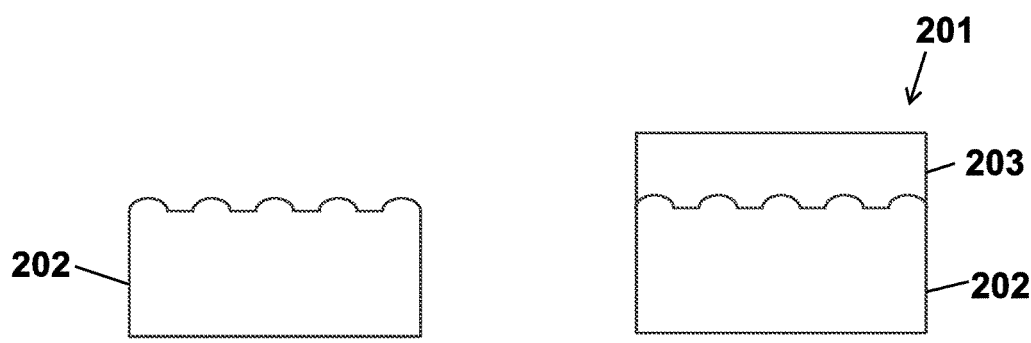
FIGS. 2A-2B are cross-sectional views of neutron generating targets, in accordance with some embodiments of the present disclosure.
Figure 2B:
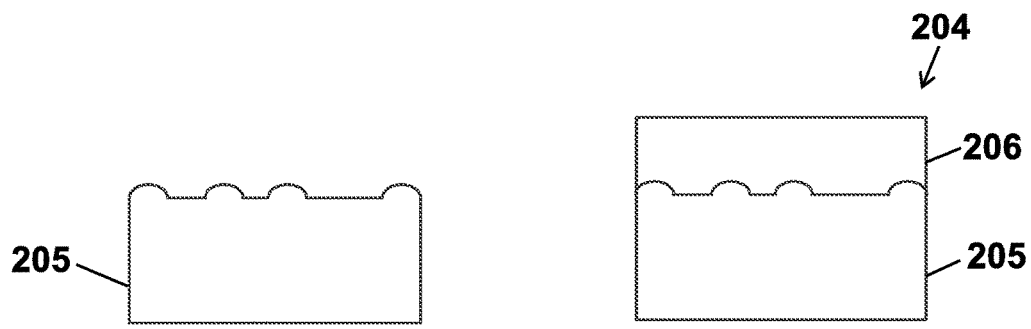

The roughness or features created on the substrate surface can be periodic or non-periodic. In some embodiments, the average pitch of the features can be between about 1 µm and about 10 µm. The depth/height of the features can be between about 5 µm and about 20 µm. FIGS. 2A-2B shows cross-section views of targets according to some embodiments of the present disclosure. As shown in FIG. 2A, target substrate 202 can be modified to have periodic surface features with a fixed pitch. As shown in FIG. 2B, target substrate 205 can be modified to have non-periodic surface features. The average pitch of the surface features can be between 1 µm and 10 µm. The height of the surface features can be between 5 µm and 20 µm.

After the surface is modified, the target substrate can be cleaned thoroughly to remove any debris. Then a neutron source layer can be disposed on the target substrate. The neutron source layer can be lithium, beryllium, graphite (carbon), or other materials, depending on different neutron producing reactions. The neutron source layer can be disposed onto the target substrate surface by pressing, evaporation, or other methods, to make sure the neutron source layer has a close contact with the target substrate surface. For example, lithium can be pressed onto the substrate. In some embodiments, the thickness of the lithium layer can be about 100 µm to about 200 µm for a neutron producing reaction with a proton energy of between about 2 MeV and about 3 MeV.

Next the assembly of target substrate and neutron source layer can be heated to an elevated temperature. The heating can be performed with a hot-plate, a thermal chamber, or other equipment which can provide heating power. To maintain the purity of the neutron source layer and prevent any unwanted reactions, the heating can be performed in an inert environment, such as in an argon filled glove-box. The heating temperature and time duration can differ depending on the substrate material and the neutron source material. For example, for a target with lithium on a copper substrate, heating for 4 hours at 200° C. can form a good thermal and mechanical bond between the lithium and the copper. The lithium can form an amalgam with the copper, resulting in a low thermal resistance. In some embodiments, the heating procedure may not be necessary. For example, if the lithium neutron source layer is deposited on the target substrate by evaporation, the heating can be skipped because there can be a good bond between the lithium and the target substrate formed during the deposition.

Referring to FIG. 2A, a neutron source layer 203 can be disposed on the surface of target substrate 202. The whole target assembly 201 can be heated to an elevated temperature to form a good bond between the neutron source layer 203 and target substrate 202. As shown in FIG. 2B, Then a neutron source layer 206 can be disposed on the surface of target substrate 205 and the whole target assembly 204 can be heated to an elevated temperature to form a good bond between the neutron source layer 206 and target substrate 205.

An advantage of the target design with substrate surface modification described herein over the existing design in the art is that protons will not stop in the target uniformly because of the roughness of the substrate. As a result, the hydrogen will not be concentrated at a same depth. This design can reduce blistering and material exfoliation in the target.

Figure 3:
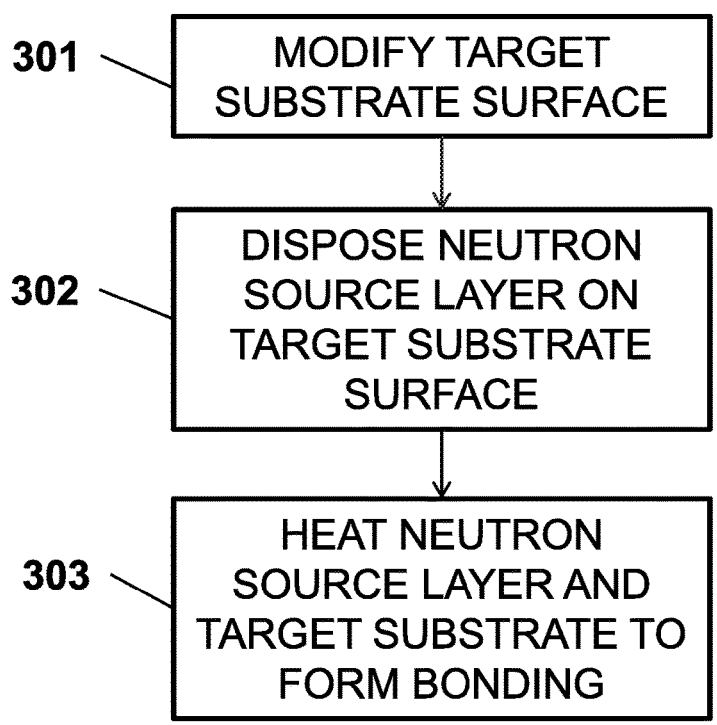
FIG. 3 is a flow chart of a method for making a neutron generating target, in accordance with some embodiments of the present disclosure.

FIG. 3 shows a flow chart describing a neutron generating target making method 300 according to some embodiments of the present disclosure. The method 300 starts with step 301 where a surface of a target substrate can be modified, either by a material removal process or a material addition process. In some embodiments, the material removal process can include abrasive blasting, etching, or polishing. In some embodiments, the material addition process can include vacuum deposition, plating, or printing. In step 302, a neutron source layer can be disposed on the surface of the target substrate by pressing, evaporation, or other techniques. Then in step 303, the whole assembly of the neutron source layer and the target substrate can be heated to an elevated temperature for a duration of time to form a good thermal and mechanical bond.

Figure 4:
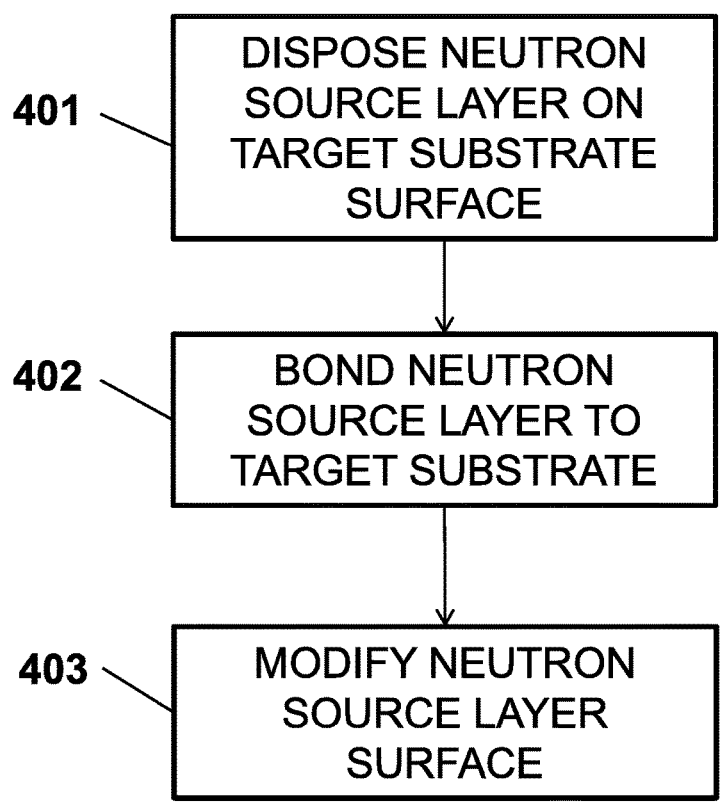
FIG. 4 is a flow chart of a method for making a neutron generating target, in accordance with some embodiments of the present disclosure.

FIG. 4 shows a flow chart describing a neutron generating target making method 400 according to some embodiments of the present disclosure. The method 400 starts with step 401 where a neutron source layer can be disposed on a target substrate. In some embodiments, the neutron source layer can be pressed onto the target substrate. In some embodiments, the neutron source layer can be deposited on the target substrate by evaporation. In step 402, the neutron source layer can be bonded to the target substrate. For example, if the neutron source layer is pressed onto the target substrate, the neutron source layer and the target substrate can be heated to an elevated temperature for a duration of time to form a bond. If the neutron source layer is deposited by evaporation, the heating procedure can be skipped. In step 403, a top surface of the neutron source layer can be modified to form one or more surface features. In some embodiment, the modification can be a material removal process which can include abrasive blasting, etching, or polishing. In some embodiment, the modification can be a material addition process which can include vacuum deposition, plating, or printing. The method 400 can create roughness on the neutron source layer surface, which can lead to variations in stopping depth of the protons so that the hydrogen concentration can be reduced. As a result, target blistering can be prevented.

The method and system described above for the $^7$Li(p,n)→$^7$Be can be extended to other neutron producing reactions with other neutron producing materials. In addition to the "near threshold" approach using a 1.9 MeV proton beam and the "above threshold" approach using a 2.5 MeV proton beam on lithium, other reactions that have been proposed for BNCT include: $^9$Be(p,n) using a 4 MeV proton beam, $^9$Be(d,n) using a 1.5 MeV deuterium beam, and $^{13}$C(d,n) using a 1.5 MeV deuterium beam. To utilize these reactions, a solid sheet of beryllium could be thermally bonded to the petals in place of the lithium and bombarded with either 4 MeV protons or 1.5 MeV deuterons. In addition, the lithium could be replaced with thin sheets of graphite or carbon to produce neutrons using the $^{13}$C(d,n) reaction.

Figure 5:
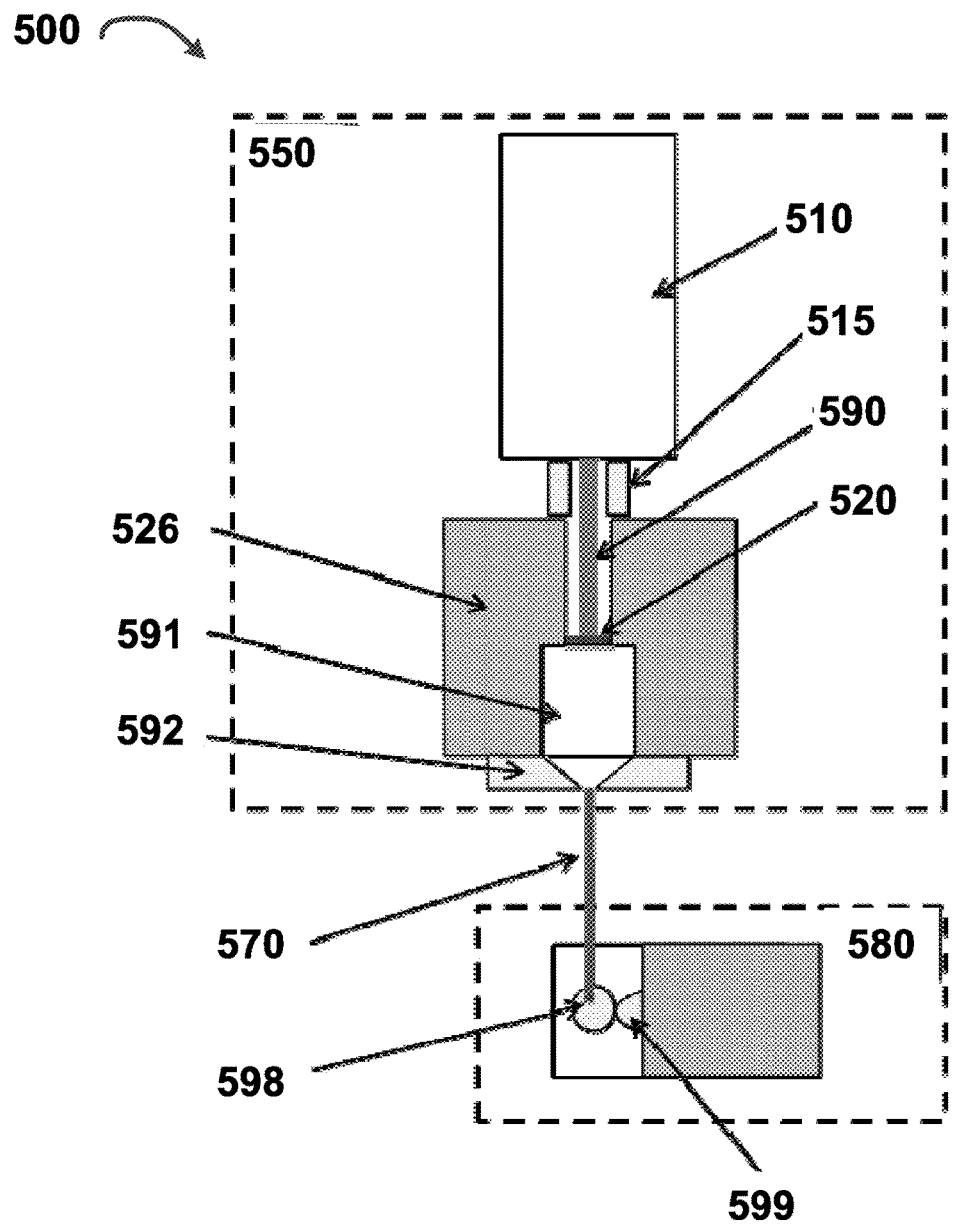
FIG. 5 is a schematic drawing, on cross-section, of a BNCT system in accordance with some embodiments of the present disclosure.

A general schematic of an embodiment of the present BNCT system and method is shown in FIG. 5. For example, referring to FIG. 5, which is not drawn to scale, BNCT system 500 includes neutron generating system 550 and patient positioning and treatment system 580. Neutron generating system 550 includes proton beam generator 510 and neutron source target 520, which is provided on a rotatable structure (not shown). Any of the rotatable structures of the present disclosure and described above can be used. Proton beam generator 510 can be provided in a variety of different positions relative to neutron source target 520, depending upon, for example, the size and design of the facility in which they are placed. Various known bending or focusing magnets can be used to direct the generated proton beam to the target.

Proton beam 590, produced by proton beam generator 510, passes through beam transport system 515, which may include, for example, various types of focusing magnets, and reacts with neutron source target 520, thereby generating neutrons, which are generally produced in multiple directions around the source depending on their energy—higher energy neutrons moving forward from the target and lower energy neutrons scattering perpendicular to or back from the source. To generate neutron beam 570 having the desired energy and direction for BNCT treatment, neutron generating system 550 further includes reflector 526, beam moderator 591, and beam collimator 592. Any neutron beam reflector, moderator, or beam collimator/delimiter known in the art can be used, and each can be positioned around the target as desired in order to capture neutrons having the desired energy range. For example, reflector 526 can be positioned around the sides and behind the target, as shown in FIG. 5, and can comprise any material known in the art that is relatively non-absorbent to neutrons, such as high atomic number material (including lead, bismuth, or alumina), or carbonaceous materials (including graphite). In this way, low energy back-scattered neutrons are reflected back into the system, thereby protecting or shielding surrounding components as well as patient 599. The forward-directed, relatively higher energy neutrons can be captured by moderator 591 (also comprising materials that are relatively non-absorbent to neutrons), in order to reduce their energy to a desired epithermal range. In this way, for example, neutrons having an initial energy of approximately 500 keV can be reduced to a final energy of from about 1 eV to about 10 keV, which is a range desirable for BNCT treatment. Suitable moderator materials are known in the art and include, for example, D$_2$O, MgF, LiF, AlF$_3$, Al, Teflon, and mixtures thereof. Finally, as shown, beam collimator 592 can be positioned after moderator 591 to produce and focus the desired neutron beam onto target 598 in patient 599.

As shown in FIG. 5, BNCT system 500 further includes patient positioning and treatment system 580 which includes equipment and controls for delivering the neutron beam to the patient. For example, a boron delivery system and protocol are used in which the chosen boron-containing treating agent is delivered to patient 599 at the prescribed dose in order to produce target 598. Control systems are used to accurately position the target to coincide with expected neutron beam path, and such control systems would be known to one skilled in the art. Additional equipment and components can also be used as needed and would also be well known in the field.

As used herein, the terms "about" and "approximately" generally mean plus or minus 10% of the value stated, e.g., a value of about 250 would include 225 to 275, and about 1,000 would include 900 to 1,100.

The foregoing description of preferred embodiments of the present disclosure has been presented for the purposes of illustration and description. It is not intended to be exhaustive or to limit the invention to the precise forms disclosed. Modifications and variations are possible in light of the above teachings, or may be acquired from practice of the invention. The embodiments presented herein were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A method for making a neutron generating target, the method comprising:
   modifying a surface of a target substrate to form one or more surface features; and
   disposing a neutron source layer on the surface of the target substrate,
   wherein the one or more surface features have a height that is less than a thickness of the neutron source layer.

2. The method of claim 1, wherein the modifying a surface of a target substrate comprises a material removal process or a material addition process.

3. The method of claim 2, wherein the material removal process comprises abrasive blasting, etching, or polishing.

4. The method of claim 2, wherein the material addition process comprises vacuum deposition, plating, or printing.

5. The method of claim 1, wherein the disposing a neutron source layer on the surface of the target substrate comprises pressing the neutron source layer on the surface of the target substrate, or depositing the neutron source layer on the surface of the target substrate by evaporation.

6. The method of claim 1, further comprising heating the neutron source layer and the target substrate to an elevated temperature for a duration of time to form a bond between the neutron source layer and the target substrate.

7. The method of claim 6, wherein the elevated temperature is between about 100 degrees Celsius and about 500 degrees Celsius.

8. The method of claim 6, wherein the duration of time is between about 0.1 hours and about 10 hours.

9. The method of claim 1, wherein the target substrate comprises at least one of copper, aluminum, titanium, molybdenum, and stainless steel.

10. The method of claim 1, wherein the neutron source layer comprises at least one of lithium, beryllium, and carbon.

11. The method of claim 1, further comprising modifying a top surface of the neutron source layer to form one or more additional surface features.

12. A neutron generating target comprising:
    a target substrate having an uneven surface wherein the uneven surface comprises one or more surface features; and
    a neutron source layer disposed on the surface of the target substrate and bonded to the target substrate
    wherein the one or more surface features have a height that is less than a thickness of the neutron source layer.

13. The target of claim 12, wherein the one or more surface features are recessed into the target substrate.

14. The target of claim 13, wherein the one or more surface features have a depth of between about 1 micron and about 50 microns.

15. The target of claim 12, wherein the one or more surface features protrude from the target substrate.

16. The target of claim 15, wherein the one or more surface features have a height of between about 1 micron and about 50 microns.

17. The target of claim 12, wherein the one or more surface features comprise a plurality of surface features with an average pitch of between about 1 micron and about 50 microns.

18. The target of claim 12, wherein the target substrate comprises at least one of copper, aluminum, titanium, molybdenum, and stainless steel.

19. The target of claim 12, wherein the neutron source layer comprises at least one of lithium, beryllium, and carbon.

20. The target of claim 12, wherein the neutron source layer has a thickness of between about 10 microns and about 500 microns.

* * * * *